United States Patent [19]

Roalstad et al.

[11] 4,262,665

[45] Apr. 21, 1981

[54] INTRAMEDULLARY COMPRESSION DEVICE

[76] Inventors: Walter L. Roalstad, Oak Creek, Star Rte. #8, Flagstaff, Ariz. 86001; Ernest W. Yeager, 19201 N. 21st Ave., Phoenix, Ariz. 85027

[21] Appl. No.: 52,822

[22] Filed: Jun. 27, 1979

[51] Int. Cl.³ .............................................. A61F 5/04
[52] U.S. Cl. ............................................... 128/92 BC
[58] Field of Search ............. 128/92 R, 92 BC, 92 B, 128/92 BA, 92 BB; 3/1.91, 1.912, 1.913

[56] References Cited

U.S. PATENT DOCUMENTS

| | | | |
|---|---|---|---|
| 3,846,846 | 11/1974 | Fischer | 128/92 BB |
| 3,986,504 | 10/1976 | Avila | 128/92 BC |
| 4,091,806 | 5/1978 | Aginsky | 128/92 BC |

FOREIGN PATENT DOCUMENTS 2840213  5/1979  Fed. Rep. of Germany ............. 3/1.91

Primary Examiner—Stephen C. Pellegrino
Attorney, Agent, or Firm—Harvey B. Jacobson

[57] ABSTRACT

A first plurality of concavo-convex disks are slidably received on one end of a bolt and inserted in the medullary cavity of one section of a fractured bone. The concave side of each disk is oriented toward the fracture site. A second group of concavo-convex disks are mounted on a threaded collar and inserted in the second section of the bone with their concave sides oriented toward the fracture site. The bolt is threadedly engaged with the threaded collar. An aperture is drilled through the bone wall in the vicinity of the bolt head. The bolt is turned thus drawing the two pairs of concavo-convex disks together producing axial pressure against the bone halves to draw the fracture tightly together. Each disk also includes a plurality of radially extending grooves for allowing normal marrow activity after the bone has healed.

11 Claims, 7 Drawing Figures

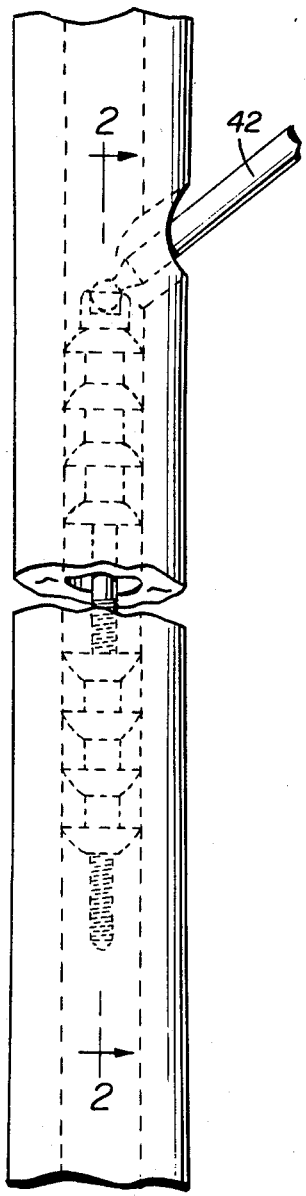
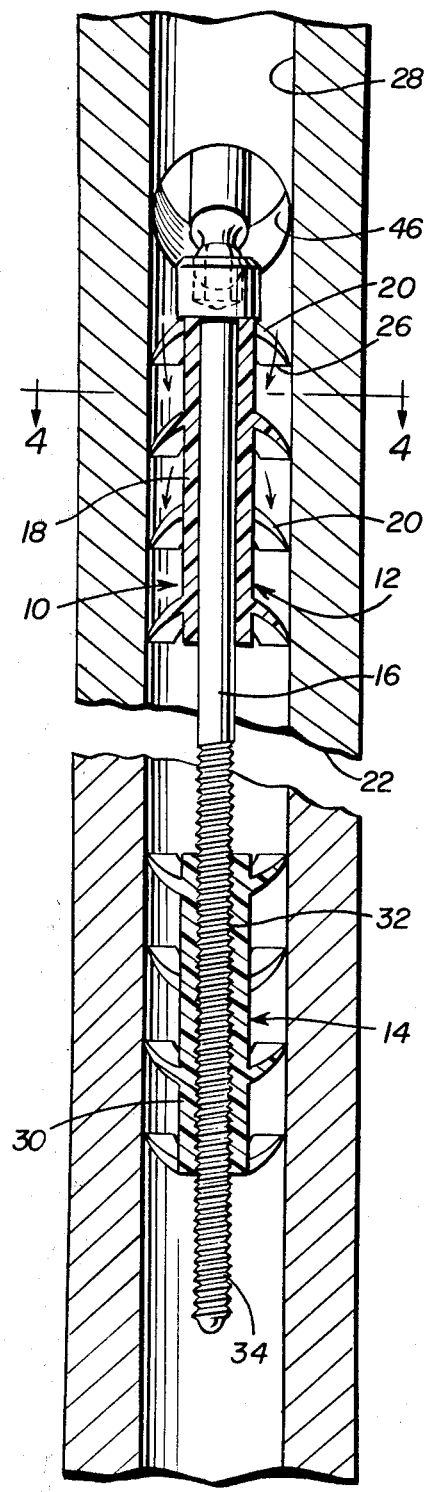
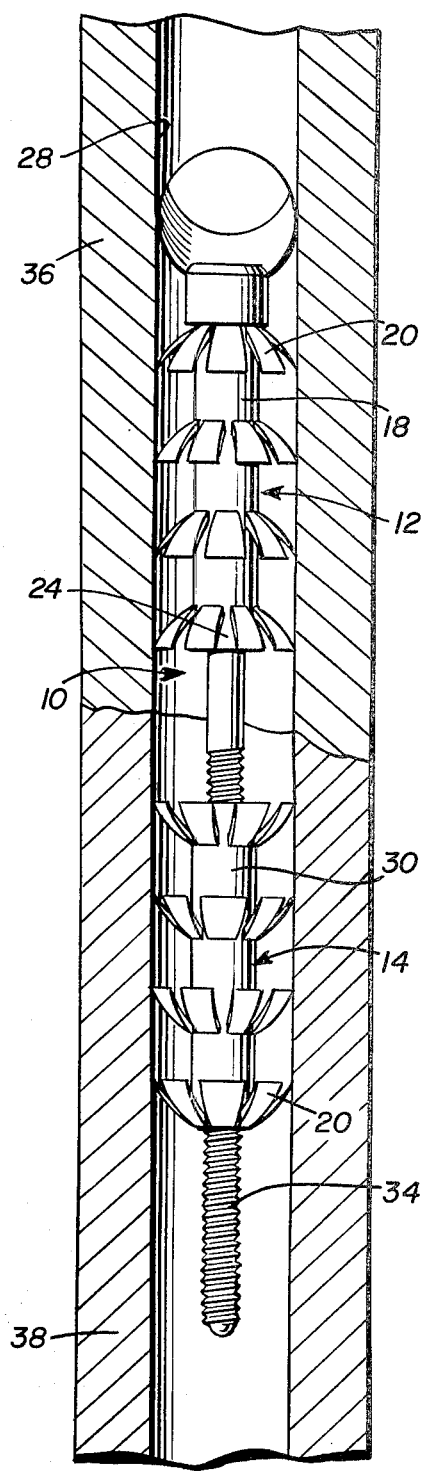
Fig. 1
Fig. 2
Fig. 3

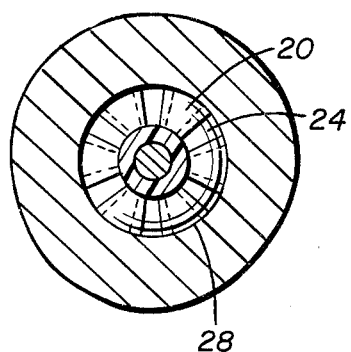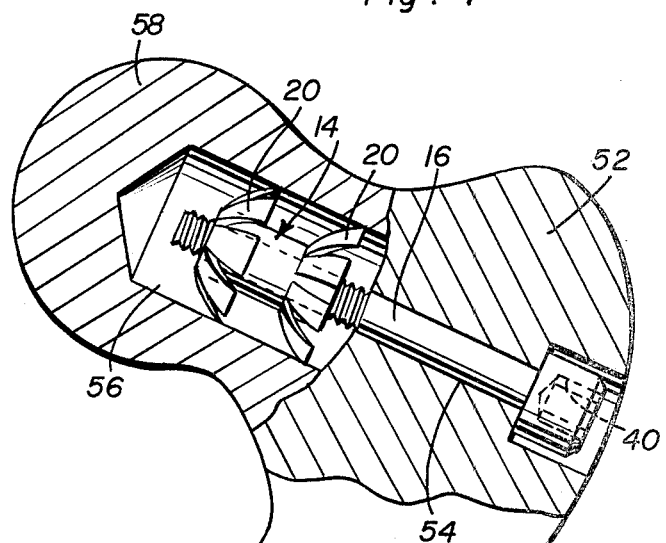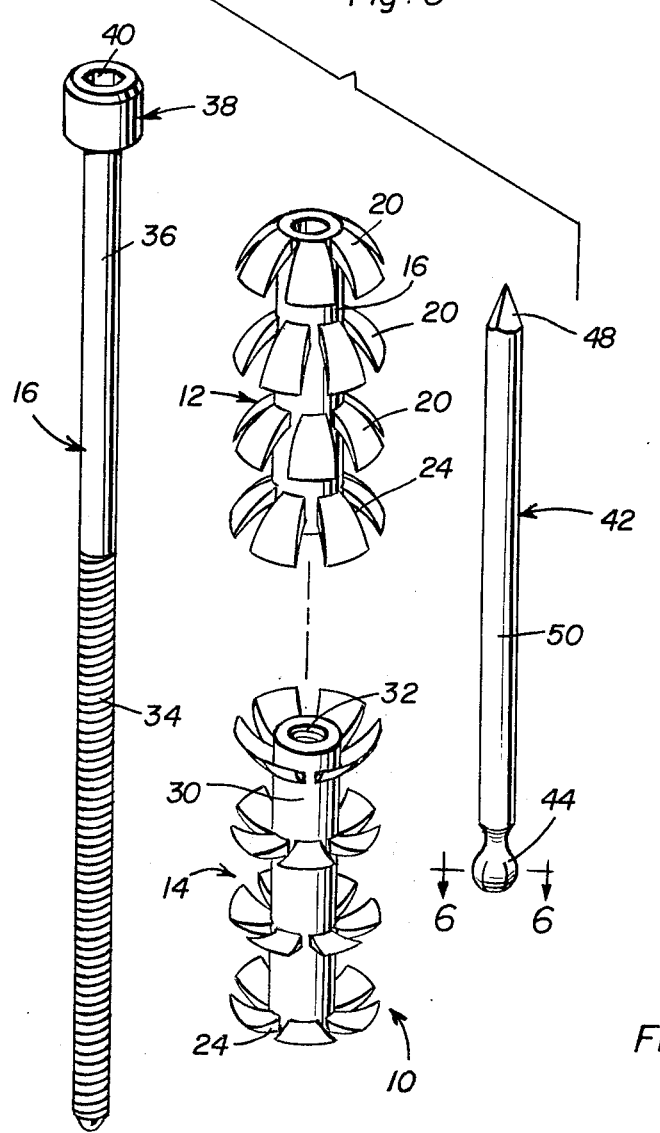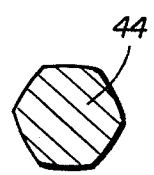

INTRAMEDULLARY COMPRESSION DEVICE

BACKGROUND OF THE INVENTION

1. Field of the Invention

This invention relates to bone fixation and compression devices.

2. Discussion of Related Art

Numerous intramedullary devices have been proposed in the past for providing both internal fixation of bone fractures as well as compression of the bone fragments at the fracture site. The normal procedure for fracture reduction when using such an intramedullary device includes drilling out a portion of the medullary canal in both the distal and proximal portions of the fractured bone. The intramedullary device is then inserted into the drilled out sections and engages the bone to draw the bone halves together. The manner of engagement between the device and the bone itself is extremely critical in that the means for engagement must provide both axial and radial stability of the bone segments. A major failing of prior intramedullary devices inheres in their failing to provide an effective engagement which both insures against radial and axial displacement of the bone halves and at the same time provides even pressure distribution to insure against bone splitting or pressure insult to the bone.

U.S. Pat. No. 3,717,146, issued Feb. 20, 1973, to Halloran, shows an intramedullary compression pin which includes conical threaded ends which are driven into the distal and proximal portions of the fractured bone and engage the cancellous bone to, in effect, tap the medullary canal and draw the rod into the bone halves. U.S. Pat. No. 3,846,846, issued Nov. 12, 1974, to Fischer, shows a hip joint prosthesis which is held in place through the use of a rod inserted in the medullary cavity of the bone and surrounded by a plurality of expansion elements. Adjacent expansion elements are telescopingly received with each inner element causing radial pressure forcing the adjacent outer element into the wall of the medullary canal. U.S. Pat. No. 4,091,806, issued May 30, 1978, to Aginsky, shows an intramedullary compression nail which includes a bolt head extending from one end of a fractured bone. The bolt extends through a sleeve having a bifurcated free end. The bifurcations are caused to separate by a threaded follower which is drawn along the bolt within the sleeve. The diverging bifurcated portions are forced into the walls of the medullary canal. U.S. Pat. No. 3,990,438, issued Nov. 9, 1976, to Pritchard, shows a bone fracture fixation and compression apparatus having a first portion containing cutting threads for anchoring within the principal bone. The other end of the device threadedly engages a screw which extends outward of the bone and is forced against the end of the bone for producing axial compression.

SUMMARY OF THE INVENTION

One object of the present invention is to provide an intramedullary compression device which is capable of conforming to the natural curvatures of the medullary canal without producing bone necrosing pressure points, thereby reducing the chance of bone splitting or pressure insult to the bone.

A further object of the present invention is to provide an intramedullary compression device which can be easily adapted to fit various sized bone marrow cavities thereby avoiding the necessity for maintaining a large stock of devices of various sizes.

An even still further object of the present invention is to provide an intramedullary compression device which is compatible with living tissues by eliminating electrolytic activity and insuring little or no temperature variation between the device and surrounding tissues.

An additional further object of the present invention is to provide an intramedullary compression device which insures radial and axial stability without impairment of endosteal circulation and also allows normal bone marrow activity to be restored in an undisturbed manner.

Another object of the present invention is to provide an intramedullary compression device wherein the compression forces are distributed circumferentially about the inner diameter of the bone as well as axially along the medullary canal.

In accordance with the above objects of the invention, an intramedullary compression device is provided which includes a pair of oppositely oriented members, each of which comprises a plurality of concavo-convex disk-like portions having circumferential ridges which engage with the inner periphery of the drilled out marrow cavity. A threaded bolt is inserted through a first of the members and threadedly engages with the second, oppositely oriented member for drawing the two members together. A plurality of radially extending grooves is disposed through each of the disks to promote restoration of normal marrow activity as well as provide flexibility for the disks. The disks distribute the forces about the marrow cavity as well as allow the device to conform to the natural curvature of the cavity.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is an elevational view showing the intramedullary compression device being inserted in the medullary canal of a fractured bone.

FIG. 2 is an elevational sectional view taken substantially along a plane passing through section line 2—2 of FIG. 1.

FIG. 3 is an elevational part sectional view showing the intramedullary compression device after insertion is complete.

FIG. 4 is a plan sectional view taken substantially along a plane passing through section line 4—4 of FIG. 2.

FIG. 5 is a perspective exploded view of the intramedullary compression device.

FIG. 6 is a sectional view of the drive pin taken substantially along a plane passing through section line 6—6 of FIG. 5.

FIG. 7 is an elevational part sectional view showing a second method of use of the intramedullary compression device.

DESCRIPTION OF THE PREFERRED EMBODIMENT

Now with reference to the drawings, an intramedullary compression device incorporating the principles and concepts of the present invention and generally referred to by the numeral 10 will be described in detail.

Initially, with reference to FIGS. 1 through 5, it can be seen that the intramedullary compression device comprises a first disk element 12 which is inserted in a first section of the fractured bone and a second disk element 14 which has a threaded interior portion for receiving the screw threads of compression screw 16. It is evident that the elements 12 and 14 are oppositely directed and caused to be forced together by the compression screw.

The first disk element 12 is made from any suitable known inert material, such as nylon, polypropylene, etc. The element includes cylindrical body portion 18 which slidably receives the compression screw 16. Formed in the exterior periphery of the element 12 and spaced longitudinally therealong are a plurality of concavo-convex disk elements 20. The disk elements 20 are oriented so that their concave surfaces are facing the fracture site 22 of the bone in which they are inserted. Each disk includes a plurality of radially extending slots 24 formed therein for increasing the resiliency of the disks and allowing the formation of blood vessels after the bone fracture has been reduced and healed. As is evident, each disk has a peripheral ridge 26 which contacts the inner circumferential surface of the drilled out marrow cavity 28 so that when axial pressure is applied to the member in a direction toward the fracture site, the ridges will dig into and grasp the marrow cavity. Of coure, insertion of the element is made from the position of the fracture site thereby causing the disks to bend inwardly facilitating insertion. Element 12 can be made in any desirable length. Of course, the more disks which are incorporated in the element, the greater will be the radial stability produced in the bone segment. Due to the spacing of the disks longitudinally of the body 18, the segment 12 can be easily cut to accommodate various sized bones. Also, since the disks 20 are flexible, the device will fit within various sized medullary cavities.

The second disk element 14 is configured similarly to element 12 except that the cylindrical body 30 of element 14 incorporates an internally threaded surface 32 which cooperates with threads 34 of the compression screw 16. Obviously, since the element 14 is disposed in the second section of the fractured bone, the disks 20 included thereon are oriented oppositely to those of element 12. In this manner, elements 12 and 14 act together to force the bone halves 36 and 38 into engagement. Element 14 also include slots 24 in the disks thereof for facilitating normal marrow activity after the bone has healed.

Further, in regard to the slots, it will be noted, especially in FIG. 4, that slots in adjacent disks 20 are offset from each other in order that the compression pressures exerted on the marrow cavity will be distributed more evenly about the circumference of the cavity. Thus it can be seen that by the use of disks incorporating slots, normal marrow activity can be encouraged while at the same time the traction for achieving compression is distributed over a broad area of the cortical bone rather than taking advantage of the weaker cancellous bone as is done in certain known devices. The segments of the disks between the slots 24 engage and grip firmly the marrow cavity on both sides of fracture site.

In order to draw the elements 12 and 14 together, compression screw 16 is provided. The compression screw is preferably made from stainless steel or any other suitable element and includes threads 34 which engage with the threads 32 of element 14. Screw 16 also has upper shaft 36 which is slidably received within the first disk element 12. A head 38 abuts against the upper end of element 12 producing axial pressure drawing it toward the threaded disk element 14. Head 38 is recessed to form a hexagonal socket 40 for the insertion of a "Allen Key" type wrench.

The wrench used to engage socket 40 is shown in FIGS. 1, 2, 5 and 6 and is generally referred to by the reference numeral 42. Wrench 42 includes rounded hexagonal head 44 which is to be inserted in socket 40. Head 44 is rounded to allow pivotal movement of the wrench in socket 40. In order to insert wrench 42 into socket 40, a hole 46, as seen in FIGS. 1 through 3, must be drilled in the bone cortex through to the medullary canal. To facilitate drilling this hole, the opposite end of wrench 42 is formed in the shape of chisel or tracor, as seen generally at 48. The shaft 50 has a smooth cylindrical surface for facilitating handling of the wrench.

With reference to FIG. 7, the versatility and adaptability of the intramedullary device of the present invention is more readily apparent. As viewed in FIG. 7, the first disk element 12 is not needed since compression screw 16 is allowed to extend out of the cortex of the bone, in this case femur 52. The chisel end 48 of wrench 42 can be used for forming a channel 54 in the femur cortex, if desired. Obviously, in view of the size of the cavity 56 necessary for retaining the ball 58 on the remainder of the femur, only two disks 20 are necessary for providing proper fixation and compression. Accordingly, the disk element 14 is cut to provide the appropriate configuration. Obviously, the socket 40 can be accessed from externally of the bone once the device is in place and proper compression can be applied to the ball 58. It will be understood that the intramedullary compression device can be changed and adapted to suit a plurality of other bone fracture configurations not shown.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An intramedullary compression device for insertion into a drilled out cavity of a bone fractured into two parts to provide fixation and compression of the bone fracture, said device comprising:

a first cavity engaging element having at least one radially extending, flexible member, said at least one radially extending flexible member being greater in diameter than its cooperating cavity and having a generally concavo-convex configuration ending in a peripheral ridge which bites into a wall of said cavity;

an axial force producing means received in said first cavity engaging element for forcing said first cavity engaging element axially toward the fracture; and bone engaging means attached to said axial force producing means for counteracting the force transmitted to said first cavity engaging element.

2. The device of claim 1 wherein said at least one radially extending flexible member has a plurality of openings formed therein for dividing said at least one radially extending flexible member into a plurality of individual flexible sections.

3. The device of claim 1 wherein said bone engaging means includes a second cavity engaging element having at least one radially extending flexible member with a diameter greater than the diameter of the cooperating cavity, the second cavity engaging element being oppositely oriented with respect to the first cavity engaging element and being connected to said axial force producing means.

4. The device of claim 3 wherein said at least one radially extending flexible member of said second cavity engaging means has a generally concavo-convex shape ending in a peripheral ridge which bites into a wall of said cavity.

5. The device of claim 4 wherein said at least one radially extending flexible member of said second cavity engaging element includes a plurality of openings formed therein for dividing the second cavity engaging element radially extending flexible member into a plurality of individual flexible sections.

6. The device of claim 1 wherein said axial force producing means comprises a threaded screw means having screw threads at one end and a head at the other end.

7. The device of claim 6 wherein one of said first and second cavity engaging elements includes threads engaging said axial force producing means and the other of said first and second cavity engaging elements slidably receives said axial force producing means and abuts against said head.

8. An intramedullary compression device for insertion into a drilled out cavity of a bone fractured into two parts to provide fixation and compression of the bone fracture, said device comprising:

a first cavity engaging element having radially extending flexible members, said radially extending flexible members being greater in diameter than their cooperating cavity and having generally a concavo-convex configuration ending in peripheral ridges which bite into walls of said cavity;

an axial force producing means received in said first cavity engaging element for forcing said first cavity engaging element axially toward the fracture; and bone engaging means attached to said axial force producing means for counteracting the force transmitted to said first cavity engaging element.

9. The device of claim 8 wherein said first cavity engaging element has at least two similar radially extending flexible members with the openings of a second radially extending flexible member being circumferentially spaced from the openings of a first radially extending flexible member for distributing forces about a circumference of the cavity.

10. The device of claim 8 wherein said bone engaging means includes a second cavity engaging element having radially extending flexible members with a diameter greater than the diameter of the cooperating cavity, the second cavity engaging element being oppositely oriented with respect to the first cavity engaging element and being connected to said axial force producing means, the radially extending flexible members of said second cavity engaging element including a plurality of openings formed therein for dividing the second cavity engaging element radially extending flexible members into a plurality of individual flexible sections.

11. The device of claim 10 wherein said second cavity engaging element has at least two similar radially extending members with the openings of the second radially extending member circumferentially spaced from the openings of said first radially extending member for distributing force about the cavity wall.

* * * * *